(12) United States Patent
Luo et al.

(10) Patent No.: US 10,173,194 B2
(45) Date of Patent: Jan. 8, 2019

(54) SYSTEMS FOR IONIC LIQUID CATALYZED ALKYLATION BASED ON A MODULAR REACTOR

(71) Applicant: Chevron U.S.A. Inc., San Ramon, CA (US)

(72) Inventors: Huping Luo, Richmond, CA (US); Arthur William Etchells, III, Philadelphia, PA (US); Donald Henry Mohr, Orinda, CA (US); Hye Kyung Cho Timken, Albany, CA (US); Moinudden Ahmed, Alamo, CA (US); Krishniah Parimi, Alamo, CA (US); Bong Kyu Chang, Novato, CA (US); Michael John Girgis, Richmond, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 16 days.

(21) Appl. No.: 15/456,863

(22) Filed: Mar. 13, 2017

(65) Prior Publication Data
US 2017/0197195 A1 Jul. 13, 2017

Related U.S. Application Data

(62) Division of application No. 14/323,262, filed on Jul. 3, 2014.

(51) Int. Cl.
| | |
|---|---|
| *B01J 19/24* | (2006.01) |
| *B01J 14/00* | (2006.01) |
| *C07C 2/62* | (2006.01) |
| *B01F 5/06* | (2006.01) |
| *B01F 5/10* | (2006.01) |

(Continued)

(52) U.S. Cl.
CPC .......... *B01J 19/24* (2013.01); *B01D 17/0208* (2013.01); *B01F 5/061* (2013.01); *B01F 5/102* (2013.01); *B01F 13/1016* (2013.01); *B01J 4/004* (2013.01); *B01J 14/00* (2013.01); *B01J 19/006* (2013.01); *B01J 19/245* (2013.01); *C07C 2/62* (2013.01); *C10G 29/205* (2013.01);
(Continued)

(58) Field of Classification Search
CPC ........ B01J 19/24; B01J 19/006; B01J 19/245; B01J 17/0208; B01J 4/004; B01J 14/00; B01F 5/102; B01F 13/1016; C07C 2/62; C10G 29/205
USPC ......................................................... 422/224
See application file for complete search history.

(56) References Cited

U.S. PATENT DOCUMENTS 2,869,844 A * 1/1959 Thomas ............... B01D 47/021
261/124
3,834,682 A * 9/1974 McPhee ................ A61M 16/16
261/123

(Continued)

FOREIGN PATENT DOCUMENTS

CN 203648 116 6/2014

*Primary Examiner* — Huy Tram Nguyen
(74) *Attorney, Agent, or Firm* — Susan Abernathy

(57) ABSTRACT

We provide systems for ionic liquid catalyzed hydrocarbon conversion that comprise a modular reactor comprising a plurality of mixer modules. The mixer modules may be arranged in series. One or more feed modules are disposed between the mixer modules. Such systems may be used for ionic liquid catalyzed alkylation reactions. Processes for ionic liquid catalyzed hydrocarbon conversion are also disclosed.

22 Claims, 7 Drawing Sheets

(51) Int. Cl.
  *B01F 13/10*   (2006.01)
  *C10G 29/20*   (2006.01)
  *B01D 17/02*   (2006.01)
  *B01J 19/00*   (2006.01)
  *B01J 4/00*    (2006.01)
  *B01F 15/02*   (2006.01)

(52) U.S. Cl.
  CPC ........... *B01F 2015/0221* (2013.01); *B01J 2219/0002* (2013.01); *B01J 2219/00777* (2013.01)

(56) References Cited

U.S. PATENT DOCUMENTS

| | | | |
|---|---|---|---|
| 4,466,741 A * | 8/1984 | Kojima | B01F 5/0615 138/37 |
| 4,965,298 A | 10/1990 | Luetzelschwab | |
| 5,138,102 A | 8/1992 | Beech, Jr. et al. | |
| 5,425,581 A * | 6/1995 | Palm | B01F 5/0473 138/37 |
| 5,869,541 A * | 2/1999 | Euzen | B01J 8/0453 518/700 |
| 6,232,515 B1 | 5/2001 | Schulz | |
| 7,285,698 B2 | 10/2007 | Liu et al. | |
| 7,484,881 B2 | 2/2009 | Schulz-Hanke et al. | |
| 7,781,548 B2 | 8/2010 | Fitzgerald et al. | |
| 7,956,230 B2 | 6/2011 | Timken et al. | |
| 8,183,425 B2 | 5/2012 | Luo et al. | |
| 8,198,499 B2 | 6/2012 | Luo et al. | |
| 8,569,561 B2 | 10/2013 | Liu et al. | |
| 8,692,048 B2 | 4/2014 | Liu et al. | |
| 2006/0004226 A1 * | 1/2006 | Machhammer | B01J 8/0453 562/526 |
| 2008/0139858 A1 | 6/2008 | Cunningham | |
| 2009/0171133 A1 * | 7/2009 | Luo | B01J 4/002 585/14 |
| 2009/0300973 A1 | 12/2009 | Ashley | |
| 2010/0010269 A1 * | 1/2010 | Kolaczkowski | B01J 8/0453 568/431 |
| 2011/0230692 A1 | 9/2011 | Timken | |
| 2011/0282114 A1 | 11/2011 | Luo et al. | |
| 2012/0178982 A1 * | 7/2012 | Liu | C07C 2/60 585/716 |
| 2013/0004378 A1 | 1/2013 | Luo et al. | |
| 2013/0287917 A1 | 1/2013 | Luo et al. | |

* cited by examiner

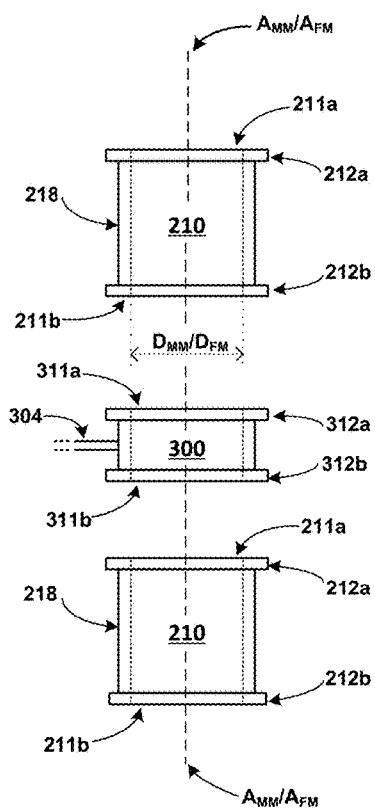
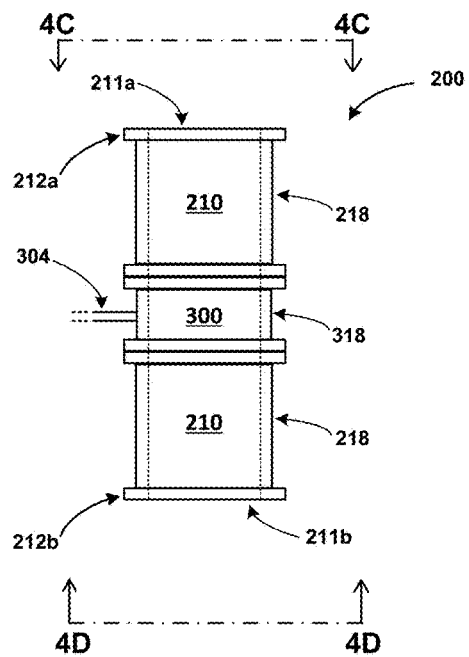
FIG. 4A          FIG. 4B
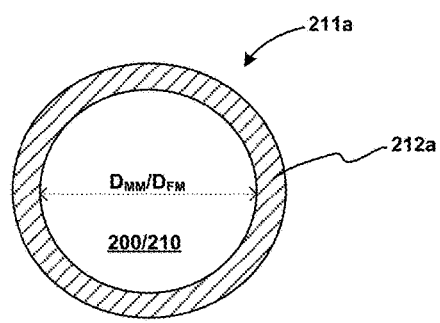
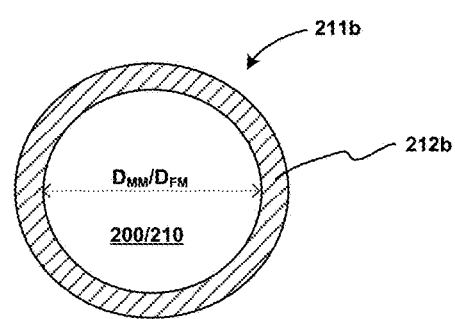
FIG. 4C          FIG. 4D

SYSTEMS FOR IONIC LIQUID CATALYZED ALKYLATION BASED ON A MODULAR REACTOR

This application is a divisional of U.S. patent application Ser. No. 14/323,262, published as US20160001255A1, filed Jul. 3, 2014, in Group Art Unit 1772; and herein incorporated in its entirety.

TECHNICAL FIELD

This disclosure relates to reactors, systems, and processes for ionic liquid catalyzed alkylation.

BACKGROUND

There is a need for apparatus, reactors, and systems for the efficient mixing of two or more immiscible liquids, such as ionic liquid catalysts and hydrocarbon feeds for ionic liquid catalyzed hydrocarbon conversion processes including ionic liquid catalyzed alkylation.

SUMMARY

In an embodiment there is provided a system for ionic liquid catalyzed hydrocarbon conversion, the system comprising a modular reactor comprising a plurality of mixer modules and one or more feed modules. The mixer modules are arranged in series, each mixer module and each feed module is vertically aligned, and each mixer module is arranged coaxially with each feed module.

In another embodiment, there is provided a system for ionic liquid catalyzed hydrocarbon conversion, the system comprising a modular reactor comprising a plurality of mixer modules and one or more feed modules, and a feed supply line in fluid communication with each feed module. The mixer modules are arranged in series, each feed module is disposed between two of the mixer modules, each mixer module and each feed module is vertically aligned, and each mixer module is coaxial with each feed module.

In yet another embodiment there is provided a system for ionic liquid catalyzed hydrocarbon conversion, the system comprising a modular reactor having a base and a top; and a circulation loop in fluid communication with the modular reactor. The circulation loop has a first loop end coupled to the base of the modular reactor. The system is configured for withdrawing reactor effluent from the base of the modular reactor into the circulation loop. The circulation loop further has a second loop end coupled to the top of the modular reactor. The system is further configured for delivering a recirculation stream to the top of the modular reactor. The modular reactor comprises a first static mixer; a first feed module disposed downstream from, and in fluid communication with, the first static mixer; and a second static mixer disposed downstream from, and in fluid communication with, the first feed module. The first static mixer is coaxial with the first feed module and the second static mixer.

In still a further embodiment there is provided a process for ionic liquid catalyzed hydrocarbon conversion, the process comprising withdrawing reactor effluent from a modular reactor, the reactor effluent comprising unreacted hydrocarbons from a hydrocarbon feed; adding ionic liquid catalyst to the reactor effluent to provide a recirculation stream; introducing the recirculation stream into a first mixer module of the modular reactor; via the first mixer module, mixing the recirculation stream to provide an ionic liquid/hydrocarbon emulsion comprising the ionic liquid catalyst and the unreacted hydrocarbons; via a first feed module, distributing the hydrocarbon feed at an elevation between the first mixer module and at least a second mixer module disposed downstream from the first mixer module; and via at least the second mixer module, mixing the hydrocarbon feed with the ionic liquid/hydrocarbon emulsion.

Further embodiments of systems and processes for ionic liquid catalyzed hydrocarbon conversion are described hereinbelow and shown in the Drawings. As used herein, the terms "comprising" and "comprises" mean the inclusion of named elements or steps that are identified following those terms, but not necessarily excluding other unnamed elements or steps.

BRIEF DESCRIPTION OF THE DRAWINGS

FIG. 4A schematically represents components of a modular reactor in exploded view as seen from the side, according to an embodiment of the present invention;

FIG. 4B schematically represents a modular reactor as seen from the side, according to an embodiment of the present invention;

FIG. 4C schematically represents a modular reactor as seen along the line 4C-4C of FIG. 4B, according to an embodiment of the present invention;

FIG. 4D schematically represents a modular reactor as seen along the line 4D-4D of FIG. 4B, according to an embodiment of the present invention;

DETAILED DESCRIPTION

Figure 1A:
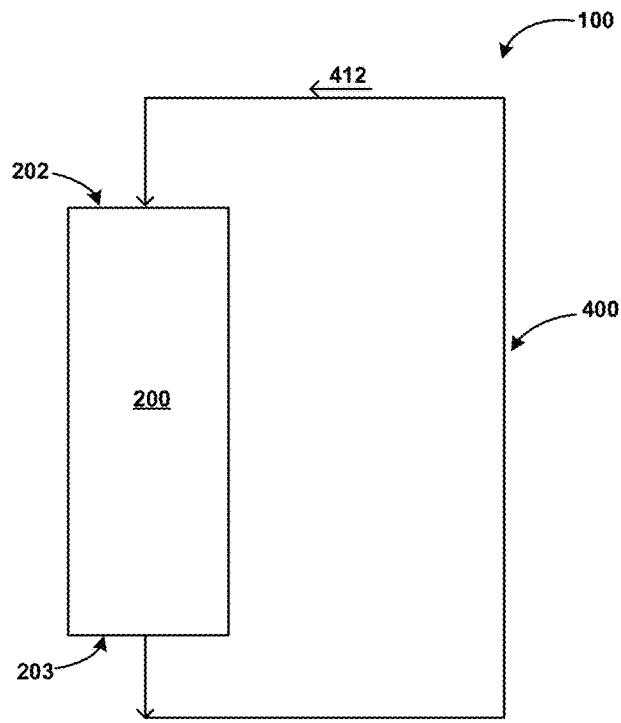
FIGS. 1A and 1B each schematically represent a system for ionic liquid catalyzed hydrocarbon conversion processes, according to embodiments of the present invention.

Ionic liquid catalysts may be useful for a range of hydrocarbon conversion reactions, including alkylation reactions for the production of alkylate, e.g., comprising gasoline blending components, and the like. Systems for ionic liquid catalyzed hydrocarbon conversion according to this disclosure may comprise a modular reactor and at least one circulation loop in fluid communication with the modular reactor, wherein each modular reactor may comprise a plurality of mixer modules arranged in series.

Modular reactors as disclosed herein provide for the rapid and thorough mixing of ionic liquid catalyst and hydrocarbon reactants so as to generate a large surface area of ionic liquid catalyst phase in an ionic liquid/hydrocarbon mixture, thereby enabling highly efficient ionic liquid catalyzed hydrocarbon conversion processes on a commercial scale. Systems for Ionic Liquid Catalyzed Alkylation Although systems may be described herein primarily with reference to ionic liquid catalyzed alkylation reactions, such systems may also be applicable to other ionic liquid catalyzed hydrocarbon conversion reactions as well as to other processes more generally.

In an embodiment, a system for ionic liquid catalyzed hydrocarbon conversion processes may comprise a modular reactor comprising a plurality of mixer modules and one or more feed modules. Each of the plurality of mixer modules may be arranged in series. In an embodiment, each of the mixer modules and each of the feed modules may be arranged vertically or upright. In an embodiment, each of the mixer modules and each of the feed modules may be vertically aligned, and each of the mixer modules may be arranged coaxially with each of the feed modules.

In an embodiment, the mixer modules may be arranged alternately with the feed modules such that each feed module is disposed between two adjacent mixer modules. The mixer modules on top of the feed modules will therefore produce highly turbulent flow field to allow rapid mixing in the feed modules. The mixer modules and the feed modules may be stacked on top of each other such that each mixer module may be in contact with at least one of the feed modules, and each feed module may be in contact with two adjacent mixer modules.

In an embodiment, the modular reactor may have one more mixer module than feed module. That is to say, for a modular reactor wherein the number of mixer modules is n, the number of feed modules may be (n−1). In an embodiment, the number of mixer modules per modular reactor may be in the range from two (2) to 10, or from two (2) to six (6), or from two (2) to four (4).

In an embodiment, each mixer module and each feed module may have a circular cross-section. In a sub-embodiment, the internal diameter of each mixer module may be the same or essentially the same as the internal diameter of each feed module. In an embodiment, each mixer module may occupy essentially the entire cross-sectional area of the modular reactor. In an embodiment, the modular reactor may be at least substantially cylindrical.

In an embodiment, each mixer module may comprise a static mixer. In an embodiment, each mixer module may comprise at least one mixer element. In a sub-embodiment, the mixer element(s) may be disposed within a cylindrical housing. In an embodiment, a surface of the mixer element may comprise a hydrophobic material. In an embodiment, each mixer module may comprise a material selected from a ceramic, an engineering plastic, and a metal alloy.

In a sub-embodiment, the mixer module may comprise one or more metal alloys, e.g., selected from Monel®, Hastelloy®, stainless steel, and tantalum-coated stainless steel. In an embodiment, the mixer module may comprise one or more engineering plastics, e.g., selected from polypropylene, Teflon®, polyvinylidene difluoride (PVDF), polyvinyl chloride (PVC), chlorinated polyvinyl chloride (CPVC), and polyoxymethylene (POM). In a sub-embodiment, a mixer module of the modular reactor may comprise a housing comprising a metal alloy and one or more mixer elements comprising an engineering plastic.

A system for ionic liquid catalyzed hydrocarbon conversion processes may further comprise a feed supply line. In an embodiment, each feed module may include a feed conduit. Each feed conduit may be in fluid communication with the feed supply line, and the system may be configured for delivering hydrocarbon feed to the modular reactor via each of the feed modules. Each feed module may be configured so as to uniformly distribute the hydrocarbon feed over the entire cross-section of the modular reactor. In an embodiment, the hydrocarbon feed may be introduced into the modular reactor at high speed sufficient to allow rapid mixing of the hydrocarbon feed stream with the liquid stream from the upper mixer module. In an embodiment, each feed module may comprise a sparger, such as a tree sparger or a ring sparger. In a sub-embodiment, such a sparger may have a diameter in the range from 40 to 100% of the internal diameter of each mixer module and of each feed module, or from 60 to 100% of the internal diameter of each mixer module and of each feed module, or from 90 to 99% of the internal diameter of each mixer module and of each feed module.

In an embodiment, the modular reactor may be configured for facile assembly and disassembly of the mixer modules to and from the feed modules. In a sub-embodiment, each mixer module may be configured for facile assembly to, and disassembly from, at least one of the feed modules; and each feed module may be configured for facile assembly to, and disassembly from, two of the mixer modules. In an embodiment, each mixer module may comprise a mixer module proximal flange at the mixer module proximal end and a mixer module distal flange at the mixer module distal end.

In an embodiment, each feed module may comprise a feed module proximal flange at the feed module proximal end and a feed module distal flange at the feed module distal end. The mixer module distal flange may be configured for coupling to a feed module proximal flange, such that the mixer module distal end may be affixed to the proximal end of an adjacent, downstream feed module. In an embodiment, such affixation of the mixer module distal end to the feed module proximal end may be reversible. The feed module distal flange may be configured for coupling to the mixer module proximal flange of an adjacent, downstream mixer module, such that the feed module distal flange may be affixed, e.g., reversibly, to the mixer module proximal flange.

A system for ionic liquid catalyzed hydrocarbon conversion may further comprise a circulation loop in fluid communication with the modular reactor. The modular reactor may have a base and a top. The circulation loop may have a first loop end coupled to the base of the modular reactor, and the circulation loop may further have a second loop end coupled to the top of the modular reactor. The system may be configured for withdrawing reactor effluent from the modular reactor via the first loop end into the circulation loop. The system may be further configured for delivering a recirculation stream to the top of the modular reactor via the second loop end. The circulation loop may comprise an ionic liquid catalyst inlet configured for adding fresh ionic liquid catalyst to withdrawn reactor effluent to provide the recirculation stream; for example, the recirculation stream may comprise withdrawn reactor effluent in combination with freshly added ionic liquid catalyst. The circulation loop may further comprise a heat exchanger configured for cooling the recirculation stream.

According to another embodiment of a system for ionic liquid catalyzed hydrocarbon conversion, the system may comprise a modular reactor comprising a plurality of mixer modules and one or more feed modules, and a feed supply line in fluid communication with each feed module. The mixer modules may be arranged in series. In an embodiment, each feed module may be disposed between two mixer modules. Each mixer module and each feed module may be vertically aligned, and each mixer module may be coaxial with each feed module. In an embodiment, each mixer module may occupy a volume in the range from 10 to 50% of the total volume of the modular reactor.

In an embodiment, each feed module may include a feed conduit. Each feed conduit may be in fluid communication with the feed supply line, and the system may be configured for delivering hydrocarbon feed to the modular reactor via each feed module. In an embodiment, each mixer module may be in fluid communication with, and in contact with, at least one feed module. In an embodiment, each feed module may be in fluid communication with, and reversibly affixed to, two mixer modules.

In an embodiment, the system may further comprise a circulation loop in fluid communication with the modular reactor. The circulation loop may have a first loop end coupled to the base of the modular reactor and a second loop end coupled to the top of the modular reactor. The system may be configured for withdrawing reactor effluent from the modular reactor via the first loop end into the circulation loop. The circulation loop may comprise an ionic liquid catalyst inlet configured for adding fresh ionic liquid catalyst to withdrawn reactor effluent to provide a recirculation stream. The circulation loop may further comprise a heat exchanger configured for cooling the recirculation stream.

In an embodiment, the plurality of mixer modules may comprise a first mixer module and at least a second mixer module disposed downstream from the first mixer module. The first mixer module may be in fluid communication with the second loop end for receiving the recirculation stream from the circulation loop. In an embodiment, the first mixer module may be configured for mixing the recirculation stream such that the ionic liquid catalyst component of the recirculation stream is dispersed into an ionic liquid/hydrocarbon emulsion, wherein the emulsion may comprise small to microscopic droplets of the ionic liquid catalyst, e.g., having a droplet diameter in the range from 1 to 1000 microns, or from 5 to 500 microns, or from 10 to 250 microns. The system may be configured for distributing the hydrocarbon feed to the modular reactor, e.g., via each feed module, between each adjacent pair of mixer modules. Each subsequent (downstream) mixer module may be configured for thoroughly and rapidly mixing the distributed hydrocarbon feed with the mixed recirculation stream emanating from the first mixer module.

According to a further embodiment of a system for ionic liquid catalyzed hydrocarbon conversion processes, the system may comprise a modular reactor and a circulation loop in fluid communication with the modular reactor. The circulation loop may have a first loop end coupled to the base of the modular reactor and a second loop end coupled to the top of the modular reactor. The system may be configured for withdrawing reactor effluent from the base of the modular reactor into the circulation loop, and the system may be further configured for delivering a recirculation stream to the top of the modular reactor.

The modular reactor may comprise a first static mixer, a second static mixer, and a first feed module disposed downstream from, and in fluid communication with, the first static mixer. The second static mixer may be disposed downstream from, and in fluid communication with, the first feed module. The first static mixer may be coaxial with the first feed module and the second static mixer.

In an embodiment, the first feed module may be reversibly affixed to, and in contact with, each of the first static mixer and the second static mixer. The modular reactor may further comprise a second feed module disposed downstream from, and in fluid communication with, the second static mixer. The modular reactor may further comprise a third static mixer disposed downstream from, and in fluid communication with, the second feed module. The first static mixer may be coaxial with the second feed module and the third static mixer. In an embodiment, each static mixer may comprise a cylindrical housing and at least one mixer element disposed within the cylindrical housing.

The second feed module may be reversibly affixed to, and in contact with, each of the second static mixer and the third static mixer. In an embodiment, the first feed module may be configured for uniformly distributing hydrocarbon feed at an elevation between the first static mixer and the second static mixer. The second feed module may be configured for distributing hydrocarbon feed at an elevation between the second static mixer and the third static mixer. The use of multiple feed modules for introducing hydrocarbon feed at different elevations of the modular reactor may serve to minimize the local olefin concentration within the modular reactor so as to provide better reactor performance and superior product(s), e.g., alkylate.

According to yet another embodiment, a process for ionic liquid catalyzed hydrocarbon conversion, e.g., isoparaffin/olefin alkylation, may be practiced using systems as disclosed herein. Such systems may comprise a modular reactor having a top and a base, and at least one circulation loop in fluid communication with the top and the base of the modular reactor. The modular reactor may comprise a plurality of mixer modules. The modular reactor may further comprise at least one feed module. Hydrocarbon feed may be delivered to the modular reactor, e.g., between adjacent mixer modules, via the at least one feed module. In an embodiment, each mixer module may be disposed vertically in series. Such systems for ionic liquid catalyzed hydrocarbon conversion may further comprise additional elements, features, and characteristics as described herein and as shown in the drawings.

In an embodiment, such a process for ionic liquid catalyzed hydrocarbon conversion may include: withdrawing reactor effluent from the modular reactor, the reactor effluent comprising unreacted hydrocarbons from a hydrocarbon feed to the modular reactor; adding ionic liquid catalyst to the reactor effluent to provide a recirculation stream; introducing the recirculation stream into a first (e.g., uppermost) mixer module of the modular reactor; via the first mixer module, mixing the recirculation stream to provide an ionic liquid/hydrocarbon emulsion comprising the ionic liquid catalyst and the unreacted hydrocarbons; via a first feed module, distributing the hydrocarbon feed at an elevation between the first mixer module and at least a second mixer module disposed downstream from the first mixer module; and via at least the second mixer module, mixing the hydrocarbon feed with the ionic liquid/hydrocarbon emulsion. In an embodiment, the ionic liquid catalyst may be added to the reactor effluent at a rate sufficient to maintain the overall ionic liquid catalyst volume in the modular reactor in the range from 0.5 to 50 vol %, or from 1 to 10 vol %, or from 2 to 6 vol %.

In an embodiment, such a process for ionic liquid catalyzed hydrocarbon conversion may further include adding a co-catalyst, or a catalyst promoter, or both a catalyst promoter and a co-catalyst, to the modular reactor. In an embodiment, such a co-catalyst may comprise an alkyl chloride. A catalyst promoter for addition to the modular reactor may comprise a hydrogen halide, such as HCl. In an embodiment, a co-catalyst and/or a catalyst promoter may be fed to the modular reactor by injection into the hydrocarbon feed, or by injection into the ionic liquid catalyst, or by direct injection into the modular reactor.

In an embodiment, the reactor effluent may be withdrawn from the base of the modular reactor via the circulation loop. Fresh ionic liquid catalyst may be added to the withdrawn reactor effluent to provide the recirculation stream, and the recirculation stream may be cooled in the circulation loop before introducing the cooled recirculation stream into the first mixer module of the modular reactor. The reactor effluent may be recirculated to the modular reactor without any attempt to separate the reactor effluent within the circulation loop. As an example, in an embodiment the circulation loop may lack a separation unit or other apparatus for phase separation of the reactor effluent or the recirculation stream. A portion of the withdrawn reactor effluent may be removed from the circulation loop for fractionation to provide an alkylate product.

In an embodiment, the flow rate through the circulation loop may be much greater than the total flow rate of the hydrocarbon feeds to reduce the temperature rise in the modular reactor and to enhance the feed dilution in the feed modules and mixer modules. In an embodiment, the flow rate through the circulation loop may be in the range from 2 to 50 times the flow rate of the hydrocarbon feed, or from 2 to 25 times the flow rate of the hydrocarbon feed, or from 4 to 10 times the flow rate of the hydrocarbon feed.

The step of mixing the recirculation stream via the first mixer module may comprise contacting the unreacted hydrocarbons with the ionic liquid catalyst in the first mixer module under alkylation conditions to provide an alkylate product. The step of mixing the hydrocarbon feed with the ionic liquid/hydrocarbon emulsion via at least the second mixer module may comprise contacting the hydrocarbon feed with the ionic liquid catalyst in at least the second mixer module under alkylation conditions to provide an additional amount of the alkylate product. Any remaining unreacted hydrocarbons in at least the second mixer module may also be contacted with the ionic liquid catalyst under alkylation conditions to provide further quantities of the alkylate product. In an embodiment, each mixer module of the modular reactor may serve as an ionic liquid alkylation zone. Furthermore, in an embodiment each feed module of the modular reactor may also serve as an ionic liquid alkylation zone.

In an embodiment, the first feed module may be disposed between the first and second mixer modules, such that the first feed module is disposed downstream from the first mixer module and the second mixer module is disposed downstream from the first feed module. Flow through the modular reactor may be downward, e.g., from the first mixer module to the first feed module and the second mixer module. The first feed module may be coaxial with both the first mixer module and the second mixer module. In an embodiment, the modular reactor may comprise additional mixer modules and additional feed modules. The mixer modules may be arranged alternately with the feed modules. Each feed module may be disposed between two mixer modules such that when the number of mixer modules is n, the number of feed modules is (n−1), wherein n may be in the range from two (2) to 10, or from two (2) to six (6), or from two (2) to four (4). In an embodiment, mixer modules of the modular reactor, e.g., the first mixer module and the second mixer module, may each comprise a static mixer. In an embodiment, at least one feed module of the modular reactor, e.g., the first feed module, may comprise a sparger.

In an embodiment, the ionic liquid/hydrocarbon emulsion formed by mixing the recirculation stream in the first mixer module may comprise small to microscopic droplets of the ionic liquid catalyst, e.g., having a droplet diameter in the range from 1 to 1000 microns, or from 5 to 500 microns, or from 10 to 250 microns. Different combinations of static mixer elements and liquid linear velocities may be chosen to achieve the said range of droplet size for the ionic liquid catalyst. For example, both helical type- and plate type static mixers that are able to produce high turbulence and achieve good radial mixing may be used.

The system may be configured for distributing the hydrocarbon feed to the modular reactor, e.g., via each feed module, between each adjacent pair of mixer modules. The second mixer module and any subsequent (downstream) mixer module(s) may be configured for thoroughly mixing the distributed hydrocarbon feed with the mixed recirculation stream emanating from the first mixer module so as to maintain the ionic liquid catalyst droplet diameter within the ranges cited hereinabove.

A range of the ionic liquid catalyzed hydrocarbon conversion processes may be practiced using systems, apparatus, and processes as disclosed herein. As non-limiting examples, such hydrocarbon conversion processes may include or be selected from: paraffin alkylation, paraffin isomerization, olefin oligomerization, cracking of olefins or paraffins, and aromatic alkylation.

In an embodiment of a process for ionic liquid catalyzed paraffin alkylation, the hydrocarbon feed may comprise at least one $C_2$-$C_{10}$ olefin and at least one $C_4$-$C_{10}$ isoparaffin. In an embodiment, the ionic liquid catalyst may comprise a chloroaluminate ionic liquid. In an embodiment, the alkylation conditions may comprise a temperature in the range from −40° C. to 150° C., and a pressure in the range from atmospheric pressure to 8000 kPa. In an embodiment, the overall ionic liquid catalyst volume in the modular reactor may be maintained in the range from 0.5 to 50 vol %, or from 1 to 10 vol %, or from 2 to 6 vol %. Hydrocarbon feeds, ionic liquid catalysts, and conditions for ionic liquid catalyzed alkylation are described hereinbelow.

Systems and apparatus for ionic liquid catalyzed hydrocarbon conversion, including alkylation for gasoline production, will now be described with reference to the drawings. FIG. 1A schematically represents a system for ionic liquid catalyzed hydrocarbon conversion processes. System 100 may comprise at least one modular reactor 200 and at least one circulation loop 400. Modular reactor 200 provides for the rapid and thorough mixing of ionic liquid catalyst and hydrocarbon reactants. As an example, modular reactor 200 may generate a large surface area of the ionic liquid catalyst phase in an ionic liquid/hydrocarbon mixture, thereby providing for the highly efficient performance of ionic liquid catalyzed hydrocarbon conversion processes.

Modular reactor 200 may have a reactor top 202 and a reactor base 203. In an embodiment, modular reactor 200 may be vertically aligned having a height greater than its width. In an embodiment, modular reactor 200 may be substantially cylindrical. In an embodiment, system 100 may comprise a plurality of mixer modules 210 per modular reactor 200 (see, for example, FIGS. 2, 3, and 4A-4B). Circulation loop 400 may be in fluid communication with modular reactor 200 for withdrawing liquid (e.g., reactor effluent) from modular reactor 200 into circulation loop 400. Circulation loop 400 may further be in fluid communication with modular reactor 200 for recirculating at least a portion of the withdrawn liquid to the reactor top 202 of modular reactor 200. Although only one circulation loop 400 is shown in FIG. 1A, in an embodiment system 100 may comprise a plurality of circulation loops 400 per modular reactor 200, wherein each circulation loop 400 may be in fluid communication with modular reactor 200.

Figure 1B:
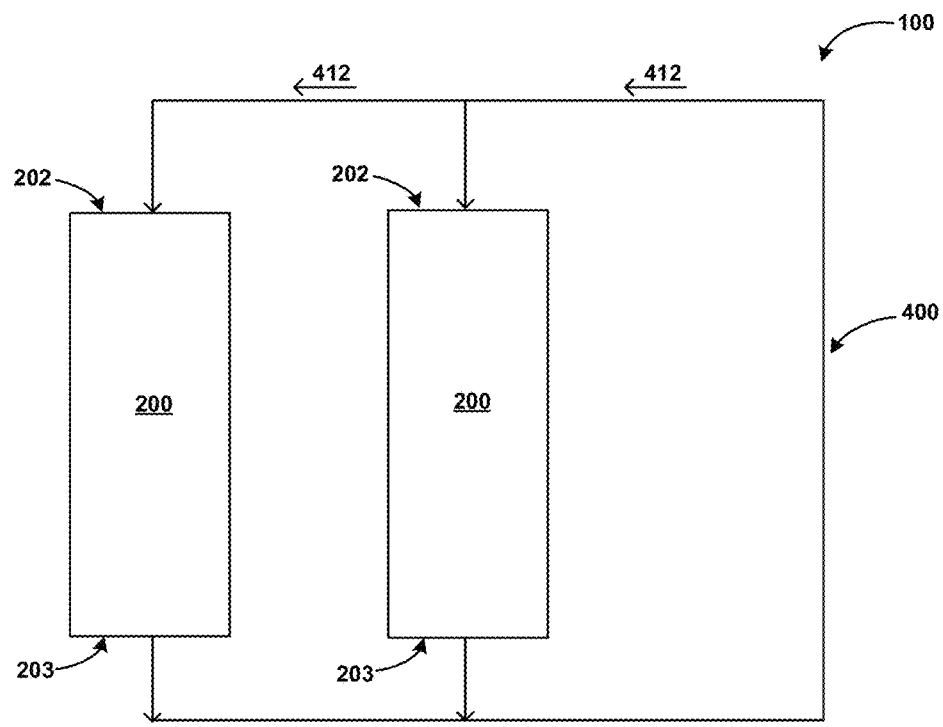

FIG. 1B schematically represents a system for ionic liquid catalyzed hydrocarbon conversion processes, wherein system 100 may comprise a plurality of modular reactors 200 per circulation loop 400. In an embodiment, the plurality of modular reactors 200 may be arranged in parallel. Each modular reactor 200 in the embodiment of FIG. 1B provides for the rapid and thorough mixing of ionic liquid catalyst and hydrocarbon reactants, substantially as described with reference to FIG. 1A, thereby providing for the highly efficient performance of ionic liquid catalyzed hydrocarbon conversion processes.

Each modular reactor 200 in the embodiment of FIG. 1B may have features, elements, and characteristics as described, for example, with reference to FIGS. 1A, 2, 3, and 4A-4B. Although two modular reactors 200 are shown in FIG. 1B, larger numbers of modular reactors may also be used per circulation loop 400. In an embodiment, the use of multiple modular reactors 200 per circulation loop 400 may serve to increase the overall reactor throughput. In an embodiment, reactor scale-up may be conveniently achieved by the addition of modular reactors 200 to system 100.

Figure 2:
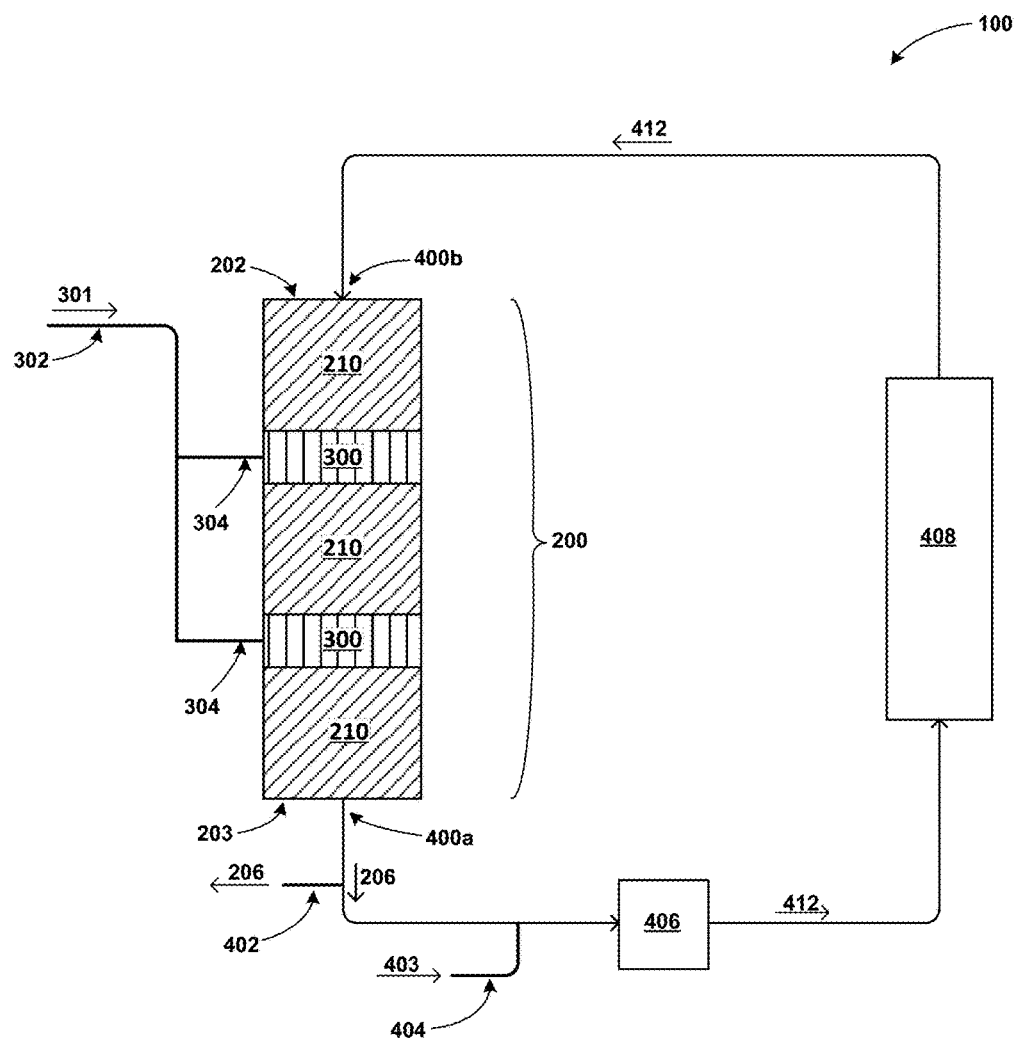
FIG. 2 schematically represents a system for ionic liquid catalyzed hydrocarbon conversion processes, according to an embodiment of the present invention.

FIG. 2 schematically represents a system 100 for ionic liquid catalyzed hydrocarbon conversion, wherein system 100 comprises a modular reactor 200 and a circulation loop 400. Modular reactor 200 may comprise a plurality of mixer modules 210 and one or more feed modules 300. Each mixer module 210 may be configured for mixing liquid(s), e.g., comprising two or more immiscible liquids, flowing through modular reactor 200. Although three mixer modules 210 are shown in FIG. 2, modular reactor 200 may comprise other numbers of mixer modules 210 (see, for example, FIG. 3).

Circulation loop 400 may comprise a first loop end 400a coupled to reactor base 203 and a second loop end 400b coupled to reactor top 202. Circulation loop 400 may further comprise a loop outlet 402, an ionic liquid catalyst inlet 404, a circulation pump 406, and a heat exchanger 408. In embodiments having a plurality of circulation loops 400 per modular reactor 200, each circulation loop 400 may have a dedicated circulation pump 406 and heat exchanger 408.

System 100 may further comprise a feed supply line 302. Each feed module 300 may include a feed conduit 304 in fluid communication with feed supply line 302. In an embodiment, each feed module 300 may be configured for introducing a hydrocarbon feed 301 into modular reactor 200, e.g., at an elevation between two adjacent, vertically stacked mixer modules 210. In an embodiment, each feed module 300 may be configured for uniformly distributing the hydrocarbon feed 301 over the entire cross-sectional area of modular reactor 200. In an embodiment, the hydrocarbon feed 301 may comprise an olefin feed stream, an isoparaffin feed stream, or a mixed olefin/isoparaffin feed, for ionic liquid catalyzed alkylation, e.g., as described hereinbelow. In an embodiment, the hydrocarbon feed 301 introduced into modular reactor 200 may comprise a liquid feed.

System 100 may be configured for withdrawing reactor effluent 206 from base 203 of modular reactor 200 into circulation loop 400. Reactor effluent 206 may comprise ionic liquid catalyst that has previously contacted the hydrocarbon feed 301 in modular reactor 200. Fresh ionic liquid catalyst 403 may be added to reactor effluent 206, within circulation loop 400, via ionic liquid catalyst inlet 404 to provide a recirculation stream 412. A portion of withdrawn reactor effluent 206 may be removed from circulation loop 400, via loop outlet 402, e.g., for fractionation thereof to provide an alkylate product.

Although only one modular reactor 200 is shown in FIG. 2, in an embodiment a plurality of modular reactors 200 may be used per circulation loop 400 (see, for example, FIG. 1B). Loop outlet 402 and ionic liquid catalyst inlet 404 may be disposed at various locations within circulation loop 400 other than as shown in FIG. 2. In an embodiment, system 100 may be configured for ionic liquid catalyzed alkylation reactions and processes. Feeds, ionic liquid catalysts, and reaction conditions for ionic liquid catalyzed alkylation are described hereinbelow.

Figure 3:
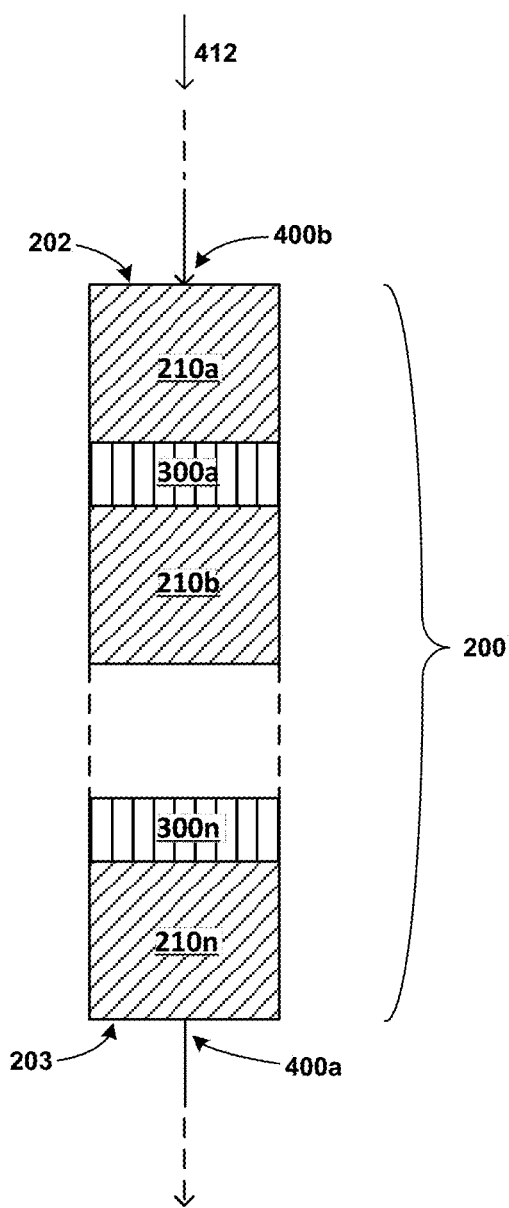
FIG. 3 schematically represents a modular reactor as seen from the side, according to an embodiment of the present invention.

FIG. 3 schematically represents a modular reactor as seen from the side. Modular reactor 200 may have a reactor top 202 and a reactor base 203. Modular reactor 200 may be in fluid communication with a first loop end 400a and a second loop end 400b of circulation loop 400 (see, for example, FIG. 2). In an embodiment, modular reactor 200 may comprise a plurality of mixer modules 210a-210n and a plurality of feed modules 300a-300n. Modular reactor 200 may receive recirculation stream 412 at the first (uppermost) mixer module 210a via second loop end 400b.

In an embodiment, mixer modules 210a-210n may be arranged alternately with feed modules 300a-300n such that each feed module 300 is disposed between two mixer modules 210. In an embodiment, all mixer modules 210a-210n and all feed modules 300a-300n may be arranged in series. In an embodiment, each of modular reactor 200, mixer modules 210a-210n, and feed modules 300a-300n may be arranged vertically or upright. In an embodiment, each mixer module 210a-210n and each feed module 300a-300n may be vertically aligned, and each of mixer modules 210a-210n may be arranged coaxially with each of feed modules 300a-300n.

In an embodiment, mixer modules 210a-210n and feed modules 300a-300n may be stacked on top of each other, such that each mixer module 210a-210n may be in contact (contiguous) with at least one of feed modules 300a-300n, and each feed module 300a-300n may be in contact (contiguous) with two of mixer modules 210a-210n. In an embodiment, modular reactor 200 may have one more mixer module 210 than feed module 300. As an example, for a modular reactor 200 having n mixer modules 210a-210n, the number of feed modules 300 may be (n−1). In an embodiment, each modular reactor 200 may typically comprise from two (2) to 10 mixer modules 210, or from two (2) to six (6) mixer modules 210, or from two (2) to four (4) mixer modules 210.

FIG. 4A schematically represents components of a modular reactor in exploded view as seen from the side; FIG. 4B schematically represents a modular reactor as seen from the side; FIG. 4C schematically represents a modular reactor as seen along the line 4C-4C of FIG. 4B; and FIG. 4D schematically represents a modular reactor as seen along the line 4D-4D of FIG. 4B. With reference to FIGS. 4A-4D, modular reactor 200 may comprise a plurality of vertically aligned mixer modules 210. Although two mixer modules 210 are shown in FIGS. 4A-4B, other numbers of mixer modules 210 may also be used (see, e.g., FIG. 3). In an embodiment, a feed module 300 may be disposed between each adjacent pair of mixer modules 210 such that when the number of mixer modules 210 is n, the number of feed modules 300 is (n−1).

In an embodiment, modular reactor 200 may be configured such that all mixer modules 210 and feed module(s) 300 are coaxial. A common axis of modular reactor 200, mixer modules 210, and feed module(s) 300 is indicated in FIG. 4A by the line labeled $A_{MM}/A_{FM}$ (wherein the mixer module axis and the feed module axis are designated as $A_{MM}$ and $A_{FM}$, respectively).

With further reference to FIGS. 4A-4D, in an embodiment each mixer module 210 may include a mixer module housing 218 and each feed module 300 may include a feed module housing 318. In an embodiment, each mixer module 210 of modular reactor 200 may have a circular cross-section, and each mixer module 210 may have the same or essentially the same internal diameter, $D_{MM}$. In an embodiment, each feed module 300 of modular reactor 200 may have a circular cross-section, and each feed module 300 may have the same or essentially the same internal diameter, $D_{FM}$. In a sub-embodiment, the internal diameter, $D_{MM}$, of each mixer module of a given modular reactor 200 may be the same or essentially the same as the internal diameter, $D_{FM}$, of each feed module. In an embodiment, each mixer module 210 may occupy essentially the entire cross-sectional area of modular reactor 200.

Each mixer module 210 may have a mixer module proximal end 211a and a mixer module distal end 211b. Each mixer module 210 may be configured for facile assembly to, and disassembly from, at least one feed module 300; and each feed module 300 may be configured for facile assembly to, and disassembly from, two mixer modules 210. In an embodiment, each mixer module 210 may comprise a mixer module proximal flange 212a at the mixer module proximal end 211a and a mixer module distal flange 212b at the mixer module distal end 211b.

In an embodiment, each feed module 300 may comprise a feed module proximal flange 312a at the feed module proximal end 311a and a feed module distal flange 312b at the feed module distal end 311b. Mixer module distal flange 212b may be configured for coupling to feed module proximal flange 312a, such that mixer module distal end 211b may be affixed to the proximal end 311a of an adjacent, downstream feed module 300. In an embodiment, such affixation of mixer module distal end 211b to feed module proximal end 311a may be reversible. Feed module distal flange 312b may be configured for coupling to mixer module proximal flange 212a of an adjacent, downstream mixer module 210, e.g., such that feed module distal end 311b may be reversibly affixed to mixer module proximal end 211a. Flanged couplings for pipes and cylindrical housings comprising metal(s), plastics or other materials, and the like are known in the art.

In an embodiment, at least one mixer module 210 of modular reactor 200 may comprise a static mixer. In a sub-embodiment, each mixer module 210 of modular reactor 200 may comprise a static mixer. In an embodiment, each mixer module 210 may comprise at least one mixer element disposed within mixer module housing 218 (see, for example, FIG. 5). Various static mixers having a broad range of characteristics may be obtained commercially.

In an embodiment, mixer modules 210 for modular reactor 200 may be selected such that a total pressure drop across modular reactor 200, from reactor top 202 to reactor base 203, is in the range from 15 to 115 psig, or from 20 to 100 psig. System 100 and modular reactor 200 may be configured to produce small to microscopic droplets of ionic liquid catalyst within mixer modules 210 of modular reactor 200. In an embodiment, such droplets of ionic liquid catalyst may have a diameter in the range from 1 to 1000 microns, or from 5 to 500 microns, or from 10 to 250 microns. Such droplets may provide not only an ionic liquid catalyst surface area that will produce a high rate of reaction and a high quality product (e.g., alkylate), but also a hydrocarbon/ionic liquid mixed phase that is conducive to subsequent phase separation downstream. The size or size range of ionic liquid droplets produced by modular reactor 200 may be selected, for example, by adjusting the flow rate across modular reactor 200 and by mixer element design.

Figure 5:
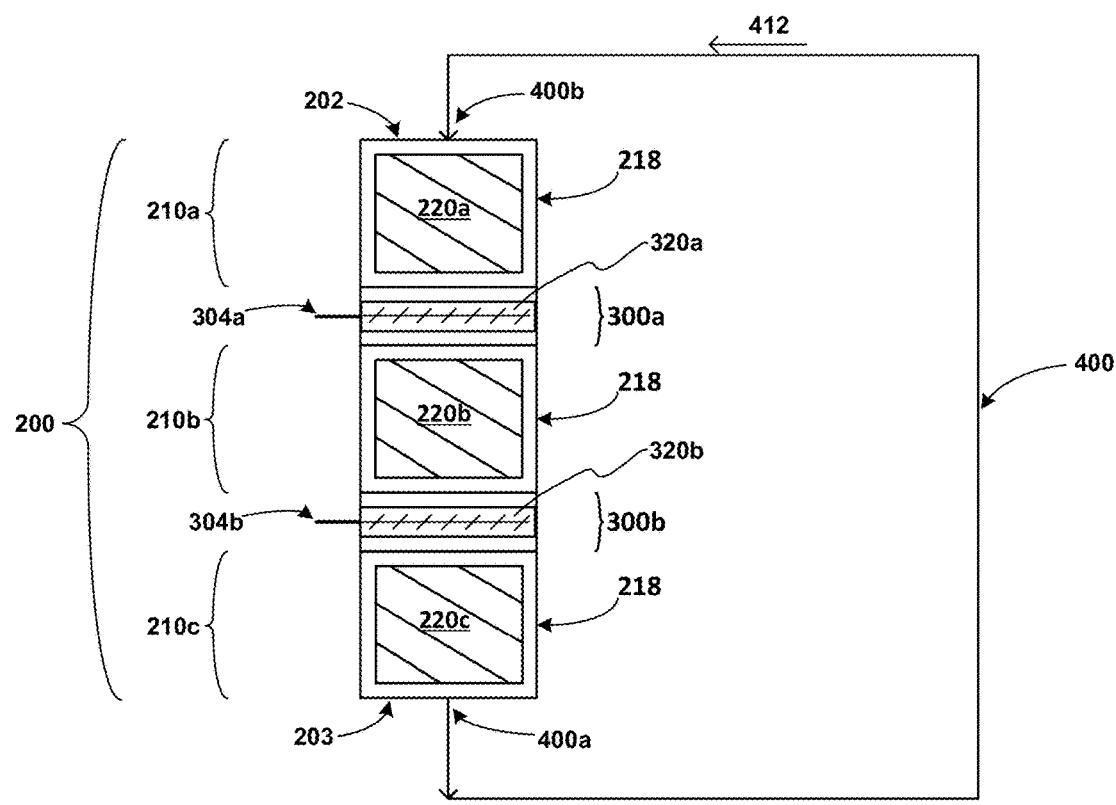
FIG. 5 schematically represents a modular reactor, as seen from the side, in combination with a circulation loop, according to an embodiment of the present invention.

FIG. 5 schematically represents a modular reactor as seen from the side. Modular reactor 200 may have a reactor top 202 and a reactor base 203. In an embodiment, modular reactor 200 may comprise a first mixer module 210a, a second mixer module 210b, and a third mixer module 210c. Mixer modules 210a-210c may comprise mixer elements 220a-220c, respectively, disposed within mixer module housing 218. Such mixer modules 210a-210c comprising one or more mixer elements may be referred to herein as static mixers. Static mixers may also be known as motionless mixers. Systems and apparatus as disclosed herein are not limited to any specific static mixer type, configuration, or design.

In an embodiment, mixer module housing 218 may comprise a cylindrical housing. In an embodiment, each of mixer modules 210a-210c may have a separate mixer module housing 218, and modular reactor 200 may be configured such that each of mixer modules 210a-210c may be removed separately (see, for example, FIGS. 4A-4B). Such modular construction of modular reactor 200 allows for the facile assembly and disassembly of modular reactor 200. Mixer modules 210a-210c may additionally include various elements, features and characteristics as described herein, for example, with reference to FIGS. 3 and 4A-4D.

With further reference to FIG. 5, modular reactor 200 may be in fluid communication with first loop end 400a of circulation loop 400 at reactor base 203 for withdrawing reactor effluent from modular reactor 200. Modular reactor 200 may further be in fluid communication with second loop end 400b of circulation loop 400 at reactor top 202 for delivering recirculation stream 412 to modular reactor 200. First mixer module 210a may be coaxial with second mixer module 210b and third mixer module 210c.

With still further reference to FIG. 5, a first feed module 300a may be disposed between first and second mixer modules, 210a and 210b, respectively, such that first feed module 300a is disposed downstream from, and in fluid communication with, first mixer module 210a. Second mixer module 210b may be disposed downstream from, and in fluid communication with, first feed module 300a. First feed module 300a may be configured for distributing hydrocarbon feed between first mixer module 210a and second mixer module 210b. First feed module 300a may be reversibly affixed to, and in contact (contiguous) with, each of first mixer module 210a and second mixer module 210b.

A second feed module 300b may be disposed between second and third mixer modules, 210b and 210c, respectively, such that second feed module 300b is disposed downstream from, and in fluid communication with, second mixer module 210b. Third mixer module 210c may be disposed downstream from, and in fluid communication with, second feed module 300b. First mixer module 210a may be coaxial with first feed module 300a and second feed module 300b. Second feed module 300b may be configured for distributing hydrocarbon feed between second mixer module 210b and third mixer module 210c. Second feed module 300b may be reversibly affixed to, and in contact with, each of second mixer module 210b and third mixer module 210c.

First feed module 300a and second feed module 300b may comprise a first feed conduit 304a and a second feed conduit 304b, respectively. First feed module 300a and second feed module 300b may further comprise a first sparger 320a and a second sparger 320b, respectively. First sparger 320a and second sparger 320b may be in fluid communication with first feed conduit 304a and second feed conduit 304b, respectively. Each of first feed conduit 304a and second feed conduit 304b may be in fluid communication with feed supply line 302 (see, for example, FIG. 2) for providing hydrocarbon feed to modular reactor 200. Although, FIG. 5 shows three mixer modules 210a-210c and two feed modules 300a, 300b, other numbers of mixer modules and feed modules are also possible (see, for example, FIG. 3).

Figure 6A:
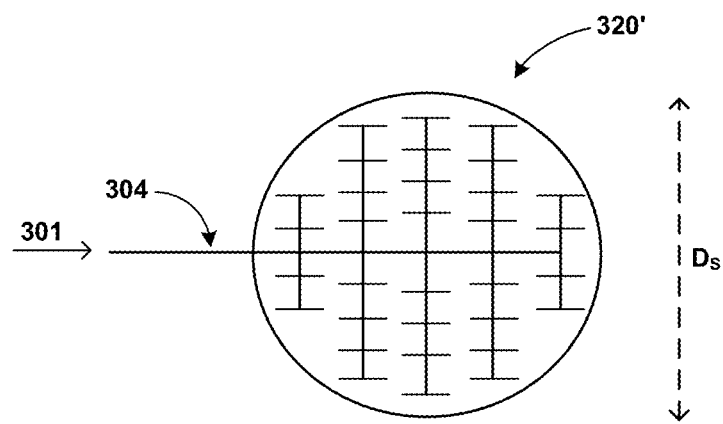
FIGS. 6A and 6B each schematically represents a sparger for distributing hydrocarbon feed to a modular reactor, as seen in reverse plan view, according to embodiments of the present invention.
Figure 6B:
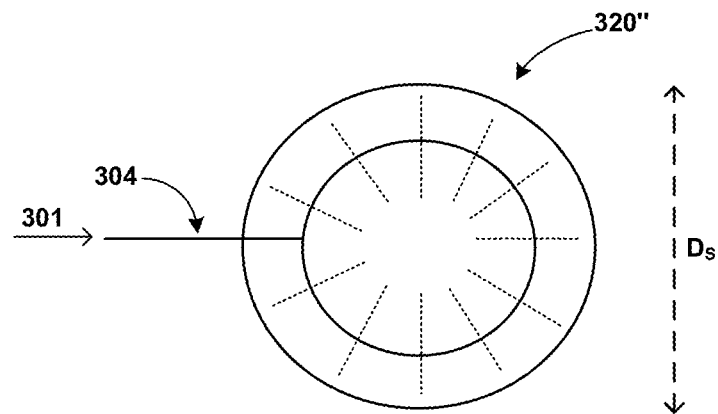

FIGS. 6A and 6B each schematically represents a sparger, as seen in reverse plan view, for distributing hydrocarbon feed 301 to a modular reactor 200. FIG. 6A schematically represents a tree sparger 320' in combination with a feed conduit 304. FIG. 6B schematically represents a ring sparger 320" in combination with a feed conduit 304. In an embodiment, one or more feed modules 300 of modular reactor 200 (e.g., feed modules 300a-300n, FIG. 3) may each comprise tree sparger 320' or ring sparger 320".

Feed conduit 304 may be in fluid communication with spargers 320'/320" and with feed supply line 302 (see, e.g., FIG. 2) for providing hydrocarbon feed 301 to spargers 320'/320". Each of spargers 320'/320" may be configured for distributing hydrocarbon feed 301 at a location upstream from an adjacent downstream mixer module 210 (see, for example, FIG. 5). In an embodiment, spargers 320'/320" may be configured for uniformly distributing the hydrocarbon feed over the entire cross-sectional area of modular reactor 200. In an embodiment, spargers 320'/320" may have a circular cross-section and a diameter $D_S$. In an embodiment, the diameter, $D_S$, of spargers 320'/320" may be in the range from 40 to 100% of the mixer module internal diameter, $D_{MM}$, or from 60 to 100% of the mixer module internal diameter, $D_{MM}$, or from 90 to 99% of the mixer module internal diameter, $D_{MM}$. In an embodiment, the mixer module internal diameter, $D_{MM}$, may be the same or essentially the same as the feed module internal diameter, $D_{FM}$.

In an embodiment, system 100 as disclosed herein may be used for ionic liquid catalyzed alkylation processes. In an embodiment, the ionic liquid catalyst may comprise, e.g., a chloroaluminate ionic liquid as described hereinbelow. In an embodiment, the hydrocarbon feed may comprise at least one of an olefin feed stream, an isoparaffin feed stream, and a mixed olefin/isoparaffin feed, for ionic liquid catalyzed alkylation, e.g., as also described hereinbelow.

Figure 7:
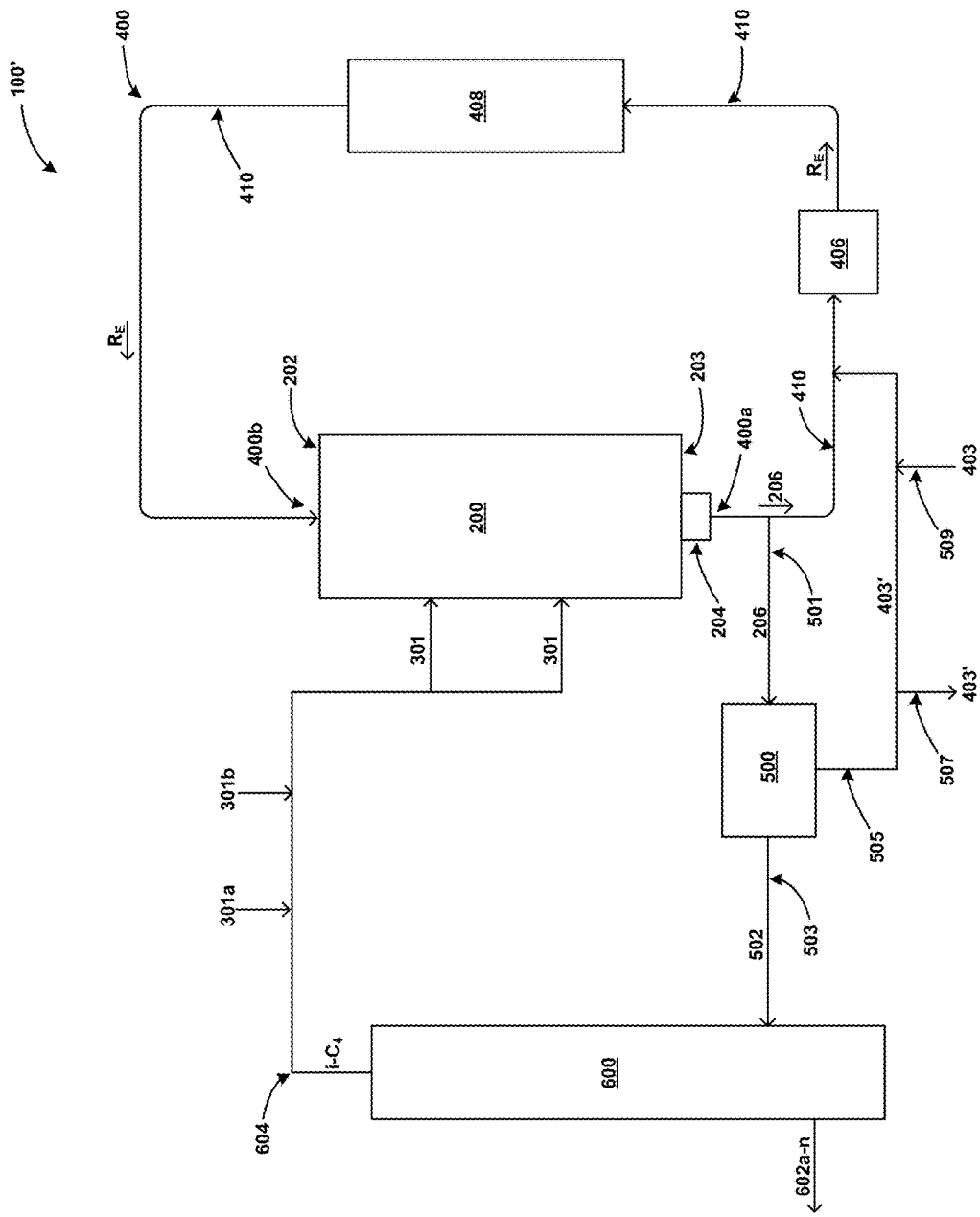
FIG. 7 schematically represents a system and process for ionic liquid catalyzed hydrocarbon conversion, according to another embodiment of the present invention.

FIG. 7 schematically represents a system and process for ionic liquid catalyzed hydrocarbon conversion, according to another embodiment. System 100' of FIG. 7 may comprise a modular reactor 200 having a reactor top 202, a reactor base 203, and a reactor outlet 204. Modular reactor 200 may comprise a plurality of mixer modules and one or more feed modules (see, for example, FIGS. 3-5). System 100' may have elements and features in common with system 100 (see, for example, FIGS. 1A-1B and 2). In modular reactor 200, at least one isoparaffin and at least one olefin may be contacted with ionic liquid catalyst under ionic liquid alkylation conditions. Ionic liquid alkylation conditions, feedstocks, and ionic liquid catalysts that may be suitable for performing ionic liquid alkylation reactions are described, for example, hereinbelow.

In an embodiment, a process for ionic liquid catalyzed hydrocarbon conversion may include adding a co-catalyst, or a catalyst promoter, or both a catalyst promoter and a co-catalyst, to modular reactor 200. In an embodiment, such a co-catalyst may comprise an alkyl chloride. A catalyst promoter for addition to the modular reactor may comprise a hydrogen halide, such as HCl. In an embodiment, a co-catalyst and/or a catalyst promoter may be fed to modular reactor 200 via the hydrocarbon feed, or via the ionic liquid catalyst feed, or by separate direct injection into modular reactor 200. The addition of co-catalyst(s) and/or catalyst promoter(s) to modular reactor 200 is not shown in the Drawings. Various methods and techniques for introducing co-catalyst(s) and/or catalyst promoter(s) to modular reactor 200 will be apparent to the skilled artisan.

System 100' may further comprise a circulation loop 400. Circulation loop 400 may comprise a first loop end 400a coupled to vessel outlet 204 and a second loop end 400b coupled to reactor top 202. In an embodiment, a first mixer module 210a may be disposed at reactor top 202 (see, for example, FIG. 3), and second loop end 400b may be coupled to, and in fluid communication with, first mixer module 210a. Circulation loop 400 may further comprise a circulation pump 406, and a heat exchanger 408. Circulation loop 400 may still further comprise at least one circulation loop conduit 410, e.g., for coupling components of circulation loop 400 to vessel outlet 204 and reactor top 202.

System 100' may still further comprise an ionic liquid/hydrocarbon (IL/HC) separator 500 in fluid communication with circulation loop 400, and a fractionation unit 600 in fluid communication with IL/HC separator 500. Reactor effluent 206 may be withdrawn from modular reactor 200 into circulation loop 400 via vessel outlet 204. A portion of the reactor effluent 206 may be fed from circulation loop 400, via a line 501, to IL/HC separator 500 for separation of the portion of reactor effluent into a hydrocarbon phase 502 and an ionic liquid phase 403'. Non-limiting examples of separation processes that can be used for such phase separation include coalescence, phase separation, extraction, membrane separation, and partial condensation. IL/HC separator 500 may comprise, for example, one or more of the following: a settler, a coalescer, a centrifuge, a cyclone, a distillation column, a condenser, and a filter. In an embodiment, IL/HC separator 500 may comprise a gravity based settler and a coalescer disposed downstream from the gravity based settler.

It can be seen from FIG. 7 that IL/HC separator 500 may be external to circulation loop 400. In an embodiment, circulation loop 400 may lack a unit or apparatus for phase separation of reactor effluent 206 or the external recirculation stream, $R_E$. Accordingly, reactor effluent 206 may be recirculated to modular reactor 200 without any attempt to separate reactor effluent 206, or the external recirculation stream, within circulation loop 400. System 100' having IL/HC separator 500 external to circulation loop 400 allows IL/HC separator 500 to be smaller than that for a system in which a separator may be used for phase separation of 100% of the withdrawn reactor effluent within a hydrocarbon recycle loop.

The hydrocarbon phase 502 from IL/HC separator 500 may be fed via a line 503 to fractionation unit 600. The hydrocarbon phase from IL/HC separator 500 may comprise alkylate components (product), as well as unreacted components of hydrocarbon feed 301, including isobutane. The alkylate components may comprise, e.g., $C_5$-$C_{11}$ alkanes, such as $C_7$-$C_8$ isoparaffins. The hydrocarbon phase from IL/HC separator 500 may be fractionated via fractionation unit 600 to provide one or more products 602a-n and an isobutane fraction. In an embodiment, products 602a-n may comprise alkylate, n-butane, and propane. In an embodiment, fractionation unit 600 may comprise one or more distillation columns.

At least a portion of the isobutane stream from fractionation unit 600 may be recycled via a line 604 to modular reactor 200. In an embodiment, the recycle isobutane may be premixed with at least one of an olefin feed stream 301*a* and a make-up isobutane feed stream 301*b* to provide a mixed hydrocarbon feed 301 for introduction into modular reactor 200. In an embodiment, modular reactor 200 may comprise a plurality of feed modules, and each feed module may separately receive hydrocarbon feed 301, e.g., via their respective feed conduit 304 (see, for example, FIG. 5). Although two inputs for hydrocarbon feed 301 to modular reactor 200 are shown in FIG. 7, other numbers and configurations are possible. In an embodiment, the number of feed modules per modular reactor 200 may be in the range from one (1) to 9, or from one (1) to five (5), or from one (1) to three (3).

The ionic liquid phase 403' from IL/HC separator 500 may be recycled to circulation loop 400 via a line 505. Make-up (e.g., fresh) ionic liquid catalyst 403 may be combined with the recycled ionic liquid catalyst via a line 509. The combined fresh and recycled ionic liquid catalyst may be injected into the reactor effluent within circulation loop 400 to provide an external recirculation stream, $R_E$, which may be cooled via heat exchanger 408. The cooled external recirculation stream may be recirculated to modular reactor 200 via circulation loop 400. In an embodiment, the ionic liquid catalyst may be added to system 100' at a rate sufficient to maintain the overall ionic liquid catalyst volume in modular reactor 200 in the range from 0.5 to 50 vol %, or from 1 to 10 vol %, or from 2 to 6 vol %.

In an embodiment, the ionic liquid phase 403' may be recycled to circulation loop 400 either directly or indirectly through a catalyst surge vessel (the latter not shown). In an embodiment, a portion of the ionic liquid phase 403' from IL/HC separator 500 may be purged or withdrawn to other vessels (not shown), via a line 507, for ionic liquid catalyst regeneration, e.g., as described hereinbelow.

Feedstocks for Ionic Liquid Catalyzed Alkylation

In an embodiment, feedstocks for ionic liquid catalyzed alkylation may comprise various olefin- and isoparaffin containing hydrocarbon streams in or from one or more of the following: a petroleum refinery, a gas-to-liquid conversion plant, a coal-to-liquid conversion plant, a naphtha cracker, a middle distillate cracker, a natural gas production unit, a LPG production unit, and a wax cracker, and the like.

Examples of olefin containing streams include FCC off-gas, coker gas, olefin metathesis unit off-gas, polyolefin gasoline unit off-gas, methanol to olefin unit off-gas, FCC light naphtha, coker light naphtha, Fischer-Tropsch unit condensate, and cracked naphtha. Some olefin containing feed streams may contain at least one olefin selected from ethylene, propylene, butylenes, pentenes, and up to $C_{10}$ olefins, i.e., $C_2$-$C_{10}$ olefins, and mixtures thereof. Such olefin containing streams are further described, for example, in U.S. Pat. No. 7,572,943, the disclosure of which is incorporated by reference herein in its entirety.

Examples of isoparaffin containing streams include, but are not limited to, FCC naphtha, hydrocracker naphtha, coker naphtha, Fisher-Tropsch unit condensate, natural gas condensate, and cracked naphtha. Such streams may comprise at least one $C_4$-$C_{10}$ isoparaffin. In an embodiment, such streams may comprise a mixture of two or more isoparaffins. In a sub-embodiment, an isoparaffin feed to the alkylation reactor during an ionic liquid catalyzed alkylation process may comprise isobutane.

Paraffin Alkylation

In an embodiment, the alkylation of a mixture of hydrocarbons may be performed in a modular reactor vessel under conditions known to produce alkylate gasoline. The modular reactor may be referred to herein as an alkylation reactor, and the modular reactor may comprise at least one alkylation zone. The alkylation conditions in the alkylation reactor are selected to provide the desired product yields and quality. The alkylation reaction in the alkylation reactor is generally carried out in a liquid hydrocarbon phase, in a batch system, a semi-batch system, or a continuous system. The catalyst volume in the alkylation reactor may be in the range of 0.5 to 50 vol %, or from 1 to 20 vol %, or from 2 to 6 vol %. In an embodiment, vigorous mixing can be attained by using one or more mixing devices per reactor, e.g., as described hereinabove, to provide contact between the hydrocarbon reactants and ionic liquid catalyst over a large surface area per unit volume of the reactor. The alkylation reaction temperature can be in the range from −40° C. to 150° C., such as −20° C. to 100° C., or −15° C. to 50° C. The alkylation pressure can be in the range from atmospheric pressure to 8000 kPa. In an embodiment the alkylation pressure is maintained at a level at least sufficient to keep the reactants in the liquid phase. The residence time of reactants in the reactor can be in the range of a second to 60 hours.

In one embodiment, the molar ratio of isoparaffin to olefin in the alkylation reactor can vary over a broad range. Generally the molar ratio of isoparaffin to olefin is in the range of from 0.5:1 to 100:1. For example, in different embodiments the molar ratio of isoparaffin to olefin is from 1:1 to 50:1, from 1.1:1 to 10:1, or from 1.1:1 to 20:1. Lower isoparaffin to olefin molar ratios will tend to produce a higher yield of higher molecular weight alkylate products, and thus can be selected when operating the alkylation reactor in a distillate mode, such as described in U.S. Patent Publication No. US20110230692A1.

Other Hydrocarbon Conversion Processes

Systems comprising a modular reactor as disclosed herein can be used for other hydrocarbon conversion processes using an acidic ionic liquid catalyst. Some examples of the hydrocarbon conversion processes include isomerization of $C_4$-$C_8$ paraffin where normal paraffins are converted to isoparaffins, oligomerization of $C_3$-$C_{30}$ olefins to produce higher molecular weight olefins, isomerization of $C_3$-$C_{30}$ olefins to shift the location of the double bond in the molecule (double bond isomerization) or shift the back-bone of the olefin molecules (skeletal isomerization), cracking of high molecular weight olefins and paraffins to low molecular paraffins and olefins, and alkylation of olefins with aromatics to form alkylaromatics.

Ionic Liquid Catalysts for Hydrocarbon Conversion Processes

In an embodiment, a catalyst for hydrocarbon conversion processes may be a chloride-containing ionic liquid catalyst comprised of at least two components which form a complex. A first component of the chloride-containing ionic liquid catalyst can comprise a Lewis Acid selected from components such as Lewis Acidic compounds of Group 13 metals, including aluminum halides, alkyl aluminum halides, gallium halides, and alkyl gallium halides, indium halides, and alkyl indium halides (see International Union of Pure and Applied Chemistry (IUPAC), version 3, October 2005, for Group 13 metals of the periodic table). Other Lewis Acidic compounds, in addition to those of Group 13 metals, can also be used. In one embodiment the first component is aluminum halide or alkyl aluminum halide. For example, aluminum trichloride can be the first component of the chloride-containing ionic liquid catalyst.

A second component comprising the chloride-containing ionic liquid catalyst is an organic salt or mixture of salts. These salts can be characterized by the general formula $Q^+A^-$, wherein $Q^+$ is an ammonium, phosphonium, boronium, iodonium, or sulfonium cation and $A^-$ is a negatively charged ion such as $Cl^-$, $Br^-$, $ClO_4^-$, $NO_3^-$, $BF_4^-$, $BCl_4^-$, $PF_6^-$, $SbF_6^-$, $AlCl_4^-$, $TaF_6^-$, $CuCl_2^-$, $FeCl_3^-$, $HSO_3^-$, $RSO_3^-$ (wherein R is an alkyl group having from 1 to 12 carbon atoms), $SO_3CF_3^-$, and $_3^-$sulfurtrioxyphenyl. In one embodiment, the second component is selected from those having quaternary ammonium or phosphonium halides containing one or more alkyl moieties having from 1 to 12 carbon atoms, such as, for example, trimethylamine hydrochloride, methyltributylammonium halide, trialkylphosphonium hydrochloride, tetraalkylphosphonium chlorides, methyltrialkylphosphonium halide or substituted heterocyclic ammonium halide compounds, such as hydrocarbyl substituted pyridinium halide compounds, for example, 1-butylpyridinium halide, benzylpyridinium halide, or hydrocarbyl substituted imidazolium halides, such as for example, 1-ethyl-3-methyl-imidazolium chloride.

In one embodiment the chloride-containing ionic liquid catalyst is selected from the group consisting of hydrocarbyl substituted pyridinium chloroaluminate, hydrocarbyl substituted imidazolium chloroaluminate, quaternary amine chloroaluminate, trialkyl amine hydrogen chloride chloroaluminate, alkyl pyridine hydrogen chloride chloroaluminate, and mixtures thereof. For example, the chloride-containing ionic liquid catalyst can be an acidic haloaluminate ionic liquid, such as an alkyl substituted pyridinium chloroaluminate or an alkyl substituted imidazolium chloroaluminate of the general formulas A and B, respectively.

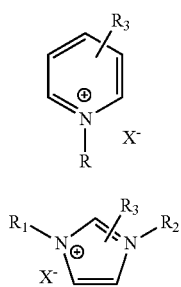

In the formulas A and B, R, $R_1$, $R_2$, and $R_3$ are H, methyl, ethyl, propyl, butyl, pentyl or hexyl group, and X is a chloroaluminate. In the formulas A and B, R, $R_1$, $R_2$, and $R_3$ may or may not be the same. In one embodiment the chloride-containing ionic liquid catalyst is N-butylpyridinium chloroaluminate. Examples of highly acidic chloroaluminates are $Al_2Cl_7^-$ and $Al_3Cl_{10}^-$.

In another embodiment the chloride-containing ionic liquid catalyst can have the general formula $RR'R''NH^+$ $Al_2Cl_7^-$, wherein R, R', and R" are alkyl groups containing from 1 to 12 carbons, and where R, R', and R" may or may not be the same.

In another embodiment the chloride-containing ionic liquid catalyst can have the general formula $RR'R''R'''P^+$ $Al_2Cl_7^-$, wherein R, R', R" and R''' are alkyl groups containing from 1 to 12 carbons, and where R, R', R" and R''' may or may not be the same.

The presence of the first component should give the chloride-containing ionic liquid a Lewis or Franklin acidic character. Generally, the greater the mole ratio of the first component to the second component, the greater is the acidity of the chloride-containing ionic liquid catalyst. The molar ratio of the first component (metal halide) to the second component (quaternary amine or quaternary phosphorus) is in the range of 2:1 to 1.1:1.

In one embodiment, the chloride-containing ionic liquid catalyst is mixed in the alkylation reactor with a hydrogen halide and/or an organic halide. The hydrogen halide or organic halide can boost the overall acidity and change the selectivity of the chloride-containing ionic liquid catalyst. The organic halide can be an alkyl halide. The alkyl halides that can be used include alkyl bromides, alkyl chlorides, alkyl iodides, and mixtures thereof. A variety of alkyl halides can be used. Alkyl halide derivatives of the isoparaffins or the olefins that comprise the feed streams in the alkylation process are good choices. Such alkyl halides include, but are not limited to, isopentyl halides, isobutyl halides, butyl halides (e.g., 1-butyl halide or 2-butyl halide), propyl halides and ethyl halides. Other alkyl chlorides or halides having from 1 to 8 carbon atoms can be also used. The alkyl halides can be used alone or in combination or with hydrogen halide. The alkyl halide or hydrogen halide is fed to the unit by injecting the alkyl halide or hydrogen halide to the hydrocarbon feed, or to the ionic liquid catalyst or to the alkylation reactor directly. The amount of HCl or alkyl chloride usage, the location of the injection and the injection method may affect the amount of organic chloride side-product formation. The use of alkyl halides to promote hydrocarbon conversion by chloride-containing ionic liquid catalysts is taught in U.S. Pat. No. 7,495,144 and in U.S. Patent Publication No. 20100298620A1.

It is believed that the alkyl halide decomposes under hydrocarbon conversion conditions to liberate Bronsted acids or hydrogen halides, such as hydrochloric acid (HCl) or hydrobromic acid (HBr). These Bronsted acids or hydrogen halides promote the hydrocarbon conversion reaction. In one embodiment the halide in the hydrogen halide or alkyl halide is chloride. In one embodiment the alkyl halide is an alkyl chloride, for example t-butyl chloride. Hydrogen chloride and/or an alkyl chloride can be used advantageously, for example, when the chloride-containing ionic liquid catalyst is a chloroaluminate.

Ionic Liquid Catalyst Regeneration

As a result of use, ionic liquid catalysts become deactivated, i.e. lose activity, and may eventually need to be replaced. However, ionic liquid catalysts are expensive and replacement adds significantly to operating expenses. Thus it is desirable to regenerate the ionic liquid catalyst on-line and reuse in the alkylation process. The regeneration of acidic ionic liquid catalysts is taught in U.S. Pat. Nos. 7,651,970, 7,674,739, 7,691,771, 7,732,363, and 7,732,364.

Alkylation processes utilizing an ionic liquid catalyst form by-products known as conjunct polymers. These conjunct polymers are highly unsaturated molecules and deactivate the ionic liquid catalyst by forming complexes with the ionic liquid catalyst. A portion of used ionic liquid catalyst from the alkylation reactor is sent to the regenerator reactor which removes the conjunct polymer from the ionic liquid catalyst and recovers the activity of the ionic liquid catalyst. The regeneration reactor contains metal components that saturates the conjunct polymers and releases the saturated polymer molecules from the ionic liquid catalyst. The regeneration can be performed either in a stirred reactor or a fixed bed reactor. For ease of operation, a fixed bed reactor is preferred even though the fixed bed regenerator reactor is more susceptible to plugging from coking, deposits of corrosion products and decomposition products derived from feed contaminants. A guard bed vessel containing adsorbent material with appropriate pore size may be added before the regeneration reactor to minimize contaminants going into the regeneration reactor.

Product Separation and Finishing

The hydrocarbon effluent product from the reactor containing ionic liquid catalyst and hydrogen halide co-catalyst may contain trace amounts of hydrogen halides or organic halides or inorganic halides. When aluminum chloride containing catalyst is used, then trace amounts of HCl, organic chlorides and inorganic chlorides may be present in the reactor effluent. HCl and organic chlorides are preferred to be captured and recycled to the alkylation reactor. Inorganic chlorides such as corrosion products or decomposition product may be captured with a filter.

The separated hydrocarbon product may still contain trace amounts of HCl, organic chlorides and inorganic chlorides. Removal of HCl and inorganic chlorides from the product are typically done by caustic washing. Chloride selective adsorbent may be used to capture the residual chlorides. Organic chloride may be converted to HCl and organic hydrocarbon by hydrogenation, cracking or hot caustic treating. Treating of products for chloride reduction is taught, for example, in US Pat. Nos. 7,538,256, 7,955,498, and 8,327,004.

EXAMPLES

Example 1

N-butylpyridinium chloroaluminate ($C_5H_5NC_4H_9Al_2Cl_7$) ionic liquid catalyst (1:2 molar ratio of N-butyl pyridinium chloride and $AlCl_3$) was used to produce alkylate shown in Example 2. The acidic ionic liquid catalyst had aluminum chloride as a metal halide component. The catalyst had the following elemental composition.

| | |
|---|---|
| Wt % Al | 12.4 |
| Wt % Cl | 56.5 |
| Wt % C | 24.6 |
| Wt % H | 3.2 |
| Wt % N | 3.3 |

Example 2

The acidic ionic liquid catalyst described in Example 1 was used to alkylate $C_3$-$C_4$ olefins with isobutane in a process unit. The alkylation was performed in a static mixer reactor system containing three mixer modules and two feed modules arranged in the sequence shown in FIG. 2. Each feed module had three spargers for hydrocarbon feed introduction. An 18:1 molar ratio of isobutane to total olefin mixture was fed to the reactor via the two feed modules. Reactor effluent was withdrawn from the base of the reactor and recirculated to the top of the reactor via a circulation loop containing the recycle flow). The relative rate of the recycle flow to the fresh hydrocarbon feed was 17:1. The pressure drop across the reactor was 50 psi. The acidic ionic liquid catalyst was fed to the circulation loop to occupy 7 vol % in the reactor. A small amount of anhydrous n-butyl chloride corresponding to 120:1 molar ratio of olefin to n-butyl chloride was added to the acidic ionic liquid catalyst in the reactor. The average residence time of the combined feeds (isobutane/olefin mixture and catalyst) in the reactor and loop was about four minutes. The outlet pressure was maintained at 190 psig and the reactor temperature was maintained at 35° C. (95° F.) using external cooling. The reactor effluent was separated with a coalescing separator into a hydrocarbon phase and an acidic ionic liquid catalyst phase.

The bulk of the separated ionic liquid catalyst was recycled back to the alkylation reactor through the circulation loop. A portion of the separated acidic ionic liquid catalyst phase was sent to a catalyst regeneration unit to maintain the conjunct polymer level in the alkylation catalyst in the range from 3 to 5 wt %.

The hydrocarbon phase was then sent to a series of three distillation columns to separate $C_5^+$, n-butane, $C_3^-$ offgas and isobutene recycle streams. The $C_5^+$ alkylate stream was analyzed using D86 laboratory distillation. Research and Motor Octane numbers were measured with an engine test. ASTM D86 distillation of the $C_5^+$ stream showed the initial boiling point of 102° F. (39 degree Celsius), $T_{50}$ boiling point of 213° F. (101 degree Celsius), $T_{90}$ boiling point of 346° F. (174 degree Celsius) and the end boiling point of 433° F. (223 degree Celsius). The resulting $C_5^+$ stream was an alkylate gasoline having a 89 RON and 89 MON. These results indicate that the in-line mixer reactor can produce high quality alkylate gasoline that can be readily blended to the refinery gasoline pool.

For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

The drawings are representational and may not be drawn to scale. Modifications of the exemplary embodiments disclosed above may be apparent to those skilled in the art in light of this disclosure. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible sub-generic combinations of the listed components and mixtures thereof.

What is claimed is:
1. A system for ionic liquid catalyzed hydrocarbon conversion, the system comprising:
a modular reactor comprising a plurality of static mixer modules and one or more feed modules, wherein:
said plurality of static mixer modules are arranged in series,
each of said plurality of static mixer modules and each of said one or more feed modules are vertically aligned, at least one of said one or more feed modules comprises a sparger that is configured for distributing a hydrocarbon feed over an entire cross-sectional area of the modular reactor,
said plurality of static mixer modules are arranged alternately with said one or more feed modules such that each of the one or more feed modules is disposed between two of said plurality of static mixer modules, and
each of said plurality of static mixer modules is arranged coaxially with each of said one or more feed modules.

2. The system according to claim 1, wherein a number of said plurality of static mixer modules is n, and a second number of said one or more feed modules is (n−1), wherein said plurality of static mixer modules are arranged alternately with said one or more feed modules such that each one of a feed module is disposed between two of said plurality of static mixer modules.

3. The system according to claim 2, wherein the number of said plurality of static mixer modules, n, is in a range from two (2) to 10.

4. The system according to claim 1, wherein:
each of said plurality of static mixer modules is in contact with at least one of said one or more feed modules, and
each of said one or more feed modules is in contact with two of said plurality of static mixer modules.

5. The system according to claim 1, wherein:
each of said plurality of static mixer modules and each of said one or more feed modules has a circular cross-section, and
each of said plurality of static mixer modules and each of said one or more feed modules has the same internal diameter.

6. The system according to claim 1, wherein each of said plurality of static mixer modules occupies essentially the entire cross-sectional area of the modular reactor.

7. The system according to claim 1, further comprising a feed supply line, wherein:
each of said one or more feed modules includes a feed conduit,
each said feed conduit is in fluid communication with the feed supply line, and
the system is configured for delivering the hydrocarbon feed to the modular reactor via each of said one or more feed modules.

8. The system according to claim 1, wherein:
each of said plurality of static mixer modules has a mixer module proximal end and a mixer module distal end, and
each of said plurality of static mixer modules comprises a mixer module proximal flange at the mixer module proximal end and a mixer module distal flange at the mixer module distal end,
each of said one or more feed modules has a feed module proximal end and a feed module distal end,
each of said one or more feed modules comprises a feed module proximal flange at the feed module proximal end and a feed module distal flange at the feed module distal end,
the mixer module distal flange is configured for coupling to the feed module proximal flange, and
the feed module distal flange is configured for coupling to the mixer module proximal flange.

9. The system according to claim 1, further comprising:
a circulation loop in fluid communication with the modular reactor, the modular reactor having a base and a top, the circulation loop having a first loop end coupled to the base of the modular reactor, and the circulation loop further having a second loop end coupled to the top of the modular reactor, the system configured for withdrawing reactor effluent from the modular reactor via the first loop end into the circulation loop, and the system further configured for delivering a recirculation stream to the top of the modular reactor via the second loop end, wherein the circulation loop comprises:
an ionic liquid catalyst inlet configured for adding fresh ionic liquid catalyst to withdrawn reactor effluent to provide the recirculation stream, and
a heat exchanger configured for cooling the recirculation stream.

10. A system for ionic liquid catalyzed hydrocarbon conversion, the system comprising:
a modular reactor comprising a plurality of mixer modules and one or more feed modules; and
a feed supply line in fluid communication with each of said one or more feed modules, wherein:
said plurality of mixer modules are arranged in series,
each of said one or more feed modules is disposed between two of said plurality of mixer modules,
at least one of said one or more feed modules comprises a sparger that is configured for distributing a hydrocarbon feed over an entire cross-sectional area of the modular reactor,
each of said plurality of mixer modules and each said one or more feed modules are vertically aligned, and
each of said plurality of mixer modules is coaxial with each of said one or more feed modules.

11. The system according to claim 10, wherein:
each said one or more feed modules includes a feed conduit,
each said feed conduit is in fluid communication with the feed supply line, and
the system is configured for delivering the hydrocarbon feed to the modular reactor via each of said one or more feed modules.

12. The system according to claim 10, wherein:
each of said plurality of mixer modules is in fluid communication with, and in contact with, at least one of said one or more feed modules, and
each of said one or more feed modules is in fluid communication with, and reversibly affixed to, two of said plurality of mixer modules.

13. The system according to claim 10, wherein:
each of said plurality of mixer modules comprises a static mixer, and
each of said one or more feed modules comprises the sparger.

14. The system according to claim 10, further comprising:
a circulation loop in fluid communication with the modular reactor, the modular reactor having a base and a top, the circulation loop having a first loop end coupled to the base of the modular reactor, and the circulation loop further having a second loop end coupled to the top of the modular reactor, the system configured for withdrawing reactor effluent from the modular reactor via the first loop end into the circulation loop, wherein the circulation loop comprises:
an ionic liquid catalyst inlet configured for adding fresh ionic liquid catalyst to withdrawn reactor effluent to provide a recirculation stream, and
a heat exchanger configured for cooling the recirculation stream.

15. The system according to claim 14, wherein:

the plurality of mixer modules comprise a first mixer module and at least a second mixer module disposed downstream from the first mixer module, the first mixer module is in fluid communication with the second loop end for receiving the recirculation stream from the circulation loop, the first mixer module is configured for mixing the recirculation stream, and the second mixer module is configured for mixing the hydrocarbon feed with the recirculation stream.

16. A system for ionic liquid catalyzed hydrocarbon conversion, the system comprising:

a modular reactor having a base and a top; and a circulation loop in fluid communication with the modular reactor, the circulation loop having a first loop end coupled to the base of the modular reactor, the system configured for withdrawing reactor effluent from the base of the modular reactor into the circulation loop, the circulation loop further having a second loop end coupled to the top of the modular reactor, and the system further configured for delivering a recirculation stream to the top of the modular reactor; wherein the modular reactor comprises:

a first static mixer, a first feed module disposed downstream from, and in fluid communication with, the first static mixer, wherein the first feed module comprises a sparger that is configured for distributing a hydrocarbon feed over an entire cross-sectional area of the modular reactor, and a second static mixer disposed downstream from, and in fluid communication with, the first feed module, wherein the first static mixer is coaxial with the first feed module and the second static mixer, and wherein the first feed module is disposed between the first static mixer and the second static mixer.

17. The system according to claim 16, wherein the modular reactor further comprises:

a second feed module disposed downstream from, and in fluid communication with, the second static mixer, and a third static mixer disposed downstream from, and in fluid communication with, the second feed module, wherein:

the first feed module is reversibly affixed to, and in contact with, each of the first static mixer and the second static mixer, the first static mixer is coaxial with the second feed module and the third static mixer, and the second feed module is reversibly affixed to, and in contact with, each of the second static mixer and the third static mixer.

18. The system according to claim 17, wherein:

the first feed module is configured for distributing the hydrocarbon feed between the first static mixer and the second static mixer, and the second feed module is configured for distributing the hydrocarbon feed between the second static mixer and the third static mixer.

19. The system according to claim 1, claim 10, or claim 16, wherein the sparger is a tree sparger or a ring sparger.

20. The system of claim 1, claim 10, or claim 16, wherein a sparger diameter is from 60 to 100% of a static mixer module internal diameter.

21. The system of claim 20, wherein the sparger diameter is from 90 to 99% of the static mixer module internal diameter.

22. The system of claim 1, or claim 10, wherein a first feed module is disposed downstream from a first static mixer module.

* * * * *